US008697901B2

(12) United States Patent
Lewis et al.

(10) Patent No.: US 8,697,901 B2
(45) Date of Patent: *Apr. 15, 2014

(54) SYNTHESIS OF ORGANOHALOSILANE MONOMERS VIA ENHANCED CLEAVAGE OF DIRECT PROCESS RESIDUE

(75) Inventors: Kenrick Martin Lewis, Flushing, NY (US); John David Neely, Clifton Park, NY (US)

(73) Assignee: Momentive Performance Materials Inc., Waterford, NY (US)

( * ) Notice: Subject to any disclaimer, the term of this patent is extended or adjusted under 35 U.S.C. 154(b) by 120 days.

This patent is subject to a terminal disclaimer.

(21) Appl. No.: 13/341,157

(22) Filed: Dec. 30, 2011

(65) Prior Publication Data

US 2013/0172594 A1 Jul. 4, 2013

(51) Int. Cl.
*C07F 7/12* (2006.01)

(52) U.S. Cl.
USPC .......................................... 556/468; 556/469

(58) Field of Classification Search
USPC .................................. 556/467, 468
See application file for complete search history.

(56) References Cited

U.S. PATENT DOCUMENTS

| | | | |
|---|---|---|---|
| 2,598,435 A | 5/1952 | Mohler et al. | |
| 2,681,355 A | 6/1954 | Barry et al. | |
| 2,709,176 A | 5/1955 | Bluestein | |
| 2,787,627 A | 4/1957 | Kuriyagawa et al. | |
| 2,842,580 A | 7/1958 | Gilbert et al. | |
| 3,432,537 A | 3/1969 | Guinet et al. | |
| 3,639,105 A | 2/1972 | Atwell et al. | |
| 4,059,608 A | 11/1977 | Calas et al. | |
| 4,070,071 A | 1/1978 | Caravito | |
| 4,298,559 A | 11/1981 | Baney et al. | |
| 4,393,229 A | 7/1983 | Ritzer et al. | |
| 4,552,973 A | 11/1985 | Feldner et al. | |
| 4,888,435 A | 12/1989 | Chadwick et al. | |
| 5,292,909 A | 3/1994 | Chadwick et al. | |
| 5,292,912 A | 3/1994 | Chadwick et al. | |
| 5,326,896 A | 7/1994 | Chadwick et al. | |
| 5,416,232 A | 5/1995 | Brendler et al. | |
| 5,502,230 A * | 3/1996 | Mautner et al. ................ | 556/468 |
| 5,627,298 A | 5/1997 | Freeburne et al. | |
| 2005/0113592 A1 | 5/2005 | Wagner et al. | |

FOREIGN PATENT DOCUMENTS

| | | |
|---|---|---|
| DE | 3208829 | 12/1982 |
| DE | 3410644 | 9/1985 |
| DE | 3436381 | 4/1986 |
| DE | 4207299 | 11/1993 |
| EP | 0861844 | 2/1998 |
| EP | 1533315 | 5/2005 |
| FR | 2427302 | 12/1979 |
| WO | WO2011008009 | 1/2011 |

OTHER PUBLICATIONS

Lewis, Kenrick M., "Selective Hydrogenolysis of Methylchlorodisilanes Using Rhenium-Containing Catalysts", ACS National Meeting, San Francisco (Apr. 1992) Abstract.
Taketa, Akira et al., "Hydrocracking of Disilanes", Chemical Abstracts, vol. 53, col. 17888i (1957).
Shiina, Kyo et al., "Cleavage of Organosubstituted Disilanes and Sisilmethylenes by Hydrogen Chloride", Chemical Abstracts, vol. 53, col. 17889b (1957).
Matsumoto, Hideyuki et al., "Conversion of Disilanes to Functional Monosilanes", Bulletin of the Chemical Society of Japan, vol. 51, No. 6, pp. 1913-1914 (1978).
Urenovitch, J. et al., "The Condensation-Polymerization of Pentamethyldisilanyl Cyanide and Related Compounds", Journal of American Chemical Society, vol. 83, pp. 3372-3375 (1963).
Urenovitch, J. et al., "Formation of Higher Silanes by the Tetramethylammonium Chloride-Catalyzed Disproportionation of Methylchlorodisilanes", Journal of the Chemical Society, pp. 5563-5564 (1963).
Matsumoto, Hideyuki et al., "A Convenient and Large Scale Synthesis of 1,1,2-Trimethyl-1,2,2-Trichlorodisilane and 1,1,2,2-Tetramethyl-1,2-Dichlorodisilane", Journal of Organometallic Chemistry, vol. 142, pp. 149-153 (1977).
Sakurai, Hideki et al., "Aluminum Chloride-Catalyzed Reactions of Organosilicon Compounds II", Tetrahedron Letters, No. 45, pp. 5493-5497 (1966).
Ishikawa, Mitsuo et al, "Preparation of Some Polysilicon Halides by Aluminum Halide Catalyzed Interchange of Methyl and Halogen on Silicon", Journal of Organometallic Chemistry, vol. 23, pp. 63-69 (1970).
Zhang, Ning et al., "Conversion of a Direct Process High-Boiling Residue to Monosilanes by a Two-Step Catalysis Approach", Res. Chem. Intermed., vol. 33, No. 7, pp. 613-622 (2007).
Garcia-Escomel, Cristina et al, "Catalytic Cleavage of the Si-Si Bond of Methylchlorodisilanes with Nucleophiles: Evidences for a Stablised Silylene Reaction Intermediate", Inorganica Chimica Acta, vol. 350, pp. 407-413 (2003).
Calas, R. et al., "Scission, Par Des Composes A Liaison", Journal of Organometallic Chemistry, vol. 74, pp. 371-376 (1974) Abstract in English.
Trandell, Roger F. et al., "A Study of the Amine-Induced Disporportionations of Various Methylchlorodisilanes", Journal of Inorganic Nuclear Chemistry, vol. 40, pp. 1305-1308 (1978).
Baney, Ronald H. et al., "Methylchloropolysilanes and Derivatives Prepared from the Redistribution of Methylchlorodisilanes", Organometallics, vol. 2, No. 7, pp. 859-864 (1983).

(Continued)

Primary Examiner — Samantha Shterengarts
Assistant Examiner — Amanda L Aguirre
(74) Attorney, Agent, or Firm — Dominick G. Vicari; Joseph S. Ostroff

(57) ABSTRACT

Discloses herein is a catalytic process for producing organohalosilane monomers from a high-boiling residue resulting from the Direct Reaction of an organohalide with silicon. The high-boiling residue contains more conventionally cleavable compounds than conventionally uncleavable compounds. The process includes heating the residue in the presence of a catalyst comprising (1) one or more heterocyclic amines and/ or one or more heterocyclic ammonium halides, and (2) one or more quaternary Group 15 onium compounds.

26 Claims, No Drawings

(56) References Cited

OTHER PUBLICATIONS

Herzog, U. et al., "Methylchlorooligosilanes as Products of the Basecatalysed Disporportionation of Various Methylchlorodisilanes", Journal of Organometallic Chemistry, vol. 507, pp. 221-228 (1996).

Perrin, D. D., "Dissociation Constants of Organic Bases in Aqueous Solution", Austrailian National University, Canberra, pp. 5-7 (1965).

Earle, Martyn J. et al., "Ionic Liquids. Green Solvents for the Future", Pure Applied Chemistry, vol. 72, No. 7, pp. 1391-1398 (2000).

Del Sesto, Rico E. et al., "Tetraalkylphosphonium-Based Ionic Liquids", Journal of Organometallic Chemistry, vol. 690, pp. 2536-2542 (2005).

Hawkins, L. G., "Gas Chromatographic Analysis of Methylchlorosilanes Produced by the Direct Reaction", Catalyzed Direct Reactions of Silicon, K. M. Lewis and D. G. Rethwisch, Editors, Elsevier Science Publishers, pp. 189-205 (1993).

* cited by examiner

SYNTHESIS OF ORGANOHALOSILANE MONOMERS VIA ENHANCED CLEAVAGE OF DIRECT PROCESS RESIDUE

CROSS REFERENCE TO RELATED APPLICATIONS

U.S. patent application Ser. No. 13/340,882 filed on even date herewith and entitled SYNTHESIS OF ORGANOHALOSILANE MONOMERS FROM CONVENTIONALLY UNCLEAVABLE DIRECT PROCESS RESIDUE is incorporated herein by reference in its entirety.

FIELD OF THE INVENTION

The present invention relates to enhanced cleavage of high-boiling by-products from the Direct Synthesis of organohalosilanes. In particular, this invention discloses the synthesis of organohalosilane monomers via the cleavage, redistribution and disproportionation of conventionally cleavable organohalodisilanes in the presence of catalysts comprising heterocyclic amines and quaternary Group 15 onium compounds.

BACKGROUND OF THE INVENTION

Alkylhalosilanes and arylhalosilanes are valuable precursors to silicones and organofunctional silanes that are used in a broad range of industries. Methykhlorosilanes and phenylchlorosilanes are particularly valuable and are the most commonly manufactured products of these classes. The primary commercial method to prepare alkylhalosilanes and arylhalosilanes is through the Rochow-Müller Direct Process (also called Direct Synthesis and Direct Reaction), in which copper-activated silicon is reacted with the corresponding organohalide in a gas-solid or slurry-phase reactor. Gaseous products and unreacted organohalide, along with fine particulates, are continuously removed from the reactor. Hot effluent exiting from the reactor comprises a mixture of copper, metal halides, silicon, silicides, carbon, gaseous organohalide, organohalosilanes, organohalodisilanes, carbosilanes and hydrocarbons. Typically this mixture is first subjected to gas-solid separation in cyclones and filters. Then the gaseous mixture and ultrafine solids are condensed in a settler or slurry tank from which the organohalide, organohalosilanes, hydrocarbons and a portion of organohalodisilanes and carbosilanes are evaporated and sent to fractional distillation to recover the organohalosilane monomers. The solids accumulated in the settler along with the less volatile silicon-containing compounds are purged periodically and sent to waste disposal or to secondary treatment such as catalytic hydrochlorination. Organohalodisilanes and carbosilanes left in the post-distillation residues are also fed to hydrochlorination.

Organohalodisilanes, organohalopolysilanes and carbosilanes, related siloxanes and hydrocarbons, either in the post-distillation residues or in the slurry purged from the reactor, boil above orgaohalosilane monomers. Collectively they are referred to as Direct Process Residue (DPR). The terms, higher boilers, high-boiling residue and disilane fraction, are also used interchangeably with DPR. DPR can account for 1 to 10 weight percent of the Direct Synthesis product mixture and, owing to the considerable accompanying tonnage, about 1 to 8 percent of the total raw material cost of the Rochow-Müller Process. Accordingly, there have been many attempts to recover organohalosilane monomers and other values from DPR through cleavage, redistribution and disproportionation processes.

Cleavage is the term used to describe the process whereby disilanes, trisilanes, polysilanes and carbosilanes are reacted to produce monomeric silanes. Hydrochlorination and hydrogenolysis are examples of cleavage processes. Redistribution is the rearrangement of groups bonded to silicon atoms such that new molecules are produced during the reaction. For example, in the equation shown below, the compounds of the class $R^1_2SiX_2$ are formed by redistribution of $R^1_3SiX$ and $R^1SiX_3$. The reverse reaction, whereby $R^1_2SiX_2$ is converted to the original reactants is called disproportionation.

$$R^1_3SiX + R^1SiX_3 \rightleftharpoons 2R^1_2SiX_2 \quad (1)$$

Illustratively, in the case of the secondary treatment of the DPR from the Direct Synthesis of methylchlorosilanes, the literature have disclosed the following: catalytic hydrochlorination as is disclosed in U.S. Pat. No. 2,598,435; U.S. Pat. No. 2,681,355; U.S. Pat. No. 2,709,176; U.S. Pat. No. 2,842,580; U.S. Pat. No. 3,432,537, U.S. Pat. No. 5,627,298, EP 861844; and H. Matsumoto, et al., *Bulletin Chemical Society Japan*, vol 51 (1978) 1913-1914; catalytic hydrochlorination with immobilized tertiary amine catalysts as disclosed in DE 4,207,299; thermal hydrochlorination as is disclosed in EP 1533315 and U.S. Pat. No. 5,292,912; and by K. Shiina, et al., *Chemical Abstracts.*, vol 53 (1957) 17889b; catalytic hydrogenolysis as is disclosed in U.S. Pat. No. 2,787,627; U.S. Pat. No. 3,639,105; U.S. Pat. No. 4,070,071; U.S. Pat. No. 4,059,608; U.S. Pat. No. 5,292,909; U.S. Pat. No. 5,326,896 as well as in K. M. Lewis, 203$^{rd}$ ACS National Meeting, San Francisco, April 1992, *Abstract INOR* 52; and A. Taketa, et al., *Chemical Abstracts*, vol 53 (1957) 17888i; catalytic redistribution/disproportionation with Lewis Acids as is disclosed in U.S. Pat. No. 4,393,229; U.S. Pat. No. 4,552,973; U.S. Pat. No. 4,888,435 as well as in J. Urenovitch, et al, *J. Amer. Chem. Soc.*, vol 83 (1963) 3372-3375, ibid. 5563-5564; H. Matsumoto, et al., *J. Organometallic Chemistry*, vol 142 (1977) pp 149-153; Sakurai, et al., *Tetrahedron Letters, #45* (1966) 5493-5497; and Ishikawa, et al., *J. Organometallic Chemistry*, vol 23 (1970) 63-69; Lewis Acid catalyzed catalytic redistribution of Direct Process Residue with methylchlorosilane monomers, including the lower boiling fraction (boiling point <43° C.) from the Direct Process, as has been disclosed in U.S. Pat. No. 4,393,229; DE 3,208,829; DE 3,436,381; DE 3,410,644; US 2005/0113592 A1 and by Zhang, et al., *Res. Chem. Intermed.*, vol 33 (2007) pp 613-622; catalytic redistribution/disproportionation with Lewis Bases as is disclosed in U.S. Pat. No. 4,298,559; U.S. Pat. No. 5,416,232; Fr. Pat. 2,427,302 as well as in R. Trandwell, et al., *J. Inorg. Nucl. Chem.*, vol 40 (1978) 1405-1410; C. Garcia-Escomel, et al., *Inorg. Chim. Acta.*, vol 350 (2003) 407-413 and R. Calas, et al., *J. Organometallic Chemistry*, vol 71 (1974) 371-376.

One limitation of the prior art processes is the inability of these processes to convert highly methylated chlorodisilanes, such as $(CH_3)_3SiSi(CH_3)_2Cl$ and $Cl(CH_3)_2SiSi(CH_3)_2Cl$, or carbosilanes such as $Cl_2CH_3Si—CH_2—Si(CH_3)_2Cl$ to organohalosilane monomers. Illustratively, Trandell et al., (*J. Inorg. Nucl. Chem.*, 40 (1978) 1305-1308) reported that $Cl(CH_3)_2SiSi(CH_3)_2Cl$ did not disproportionate in the presence of trimethylamine even when heated to 65° C. for four months and 100° C. for two months. Garcia-Escomel, et al., (*Inorg. Chim, Acta*, Vol 350 (2003) 407-413) state that $Cl(CH_3)_2SiSi(CH_3)_2Cl$ was unreactive when treated with a variety of phosphines, phosphites, phosphine oxides and tetralkylammonium halide Lewis bases at 140-150° C. According to Baney, et al., (*Organometallics*, 2 (1983) 859-864) $Cl(CH_3)_2SiSi(CH_3)_2Cl$ remains unreacted when heated with tetrabutyl phosphonium chloride up to 150° C. Herzog, et al. (*J. Organometallic Chem.* 507 (1996) 221-229) employed higher, unspecified temperatures and N-methylimidazole as catalyst and observed the formation of a white solid, characterized as $(CH_3)_2SiCl_2$ complexed with two molecules of the catalyst, and tri- and tetra-silanes.

Recently, there are disclosures that are said to produce monomeric silanes from highly methylated chlorodisilanes. For example, JP A 54-9228 discloses the hydrochlorination of $Cl(CH_3)_2SiSi(CH_3)_2Cl$ with $[(C_6H_5)_3P]_4Pd$ as catalyst to produce $(CH_3)_2SiHCl$. For the same purpose, U.S. Pat. No. 5,502,230 discloses the use of a catalyst composition consisting of Pd(0) or Pt(0) and an additive chosen from a tertiary amine, carboxylic amide, alkylurea, tertiary phosphine, phosphoric amide, quaternary ammonium halide or quaternary phosphonium halide. U.S. Pat. No. 7,655,812 discloses a method of preparing $(CH_3)_2SiHCl$ via hydrochlorination of $Cl(CH_3)_2SiSi(CH_3)_2Cl$ comprising the use of Pd(0), a tertiary amine and a tertiary phosphine in which at least one of the hydrocarbyl groups is a functionalized aryl group. However, all these processes require the use of expensive noble metals in the catalyst compositions thus making them too expensive to be commercially practicable.

Furthermore, even for conventionally cleavable DPR, the monomers produced by the prior art processes tend to contain more $CH_3SiCl_3$ monomer than otherwise would be desirable. It is generally agreed that the organohalosilane monomers of general formula $R^1SiX_3$ are less valuable than those of general formula, $R^1{}_2SiX_2$, $R^1{}_3SiX$, $R^1SiHX_2$ and $R^1{}_2SiHX$. In the case of methylchlorosilanes, the compounds can be ranked in value based on selling prices of commercial quantities or of smaller amounts for laboratory research. Using prices published on the internet or in specialty chemical catalogs, such as Gelest, Inc., the value ranking of the methylchloro-silane monomers is $(CH_3)_2SiHCl > CH_3SiHCl_2 > (CH_3)_3SiCl > (CH_3)_2SiCl_2 > CH_3SiCl_3$. In current commercial practice, the high-boiling liquid residue from the methylchlorosilane Direct Process is reacted with HCl in the presence of a tertiary amine catalyst, such as tri(n-butyl)amine, at temperatures in the range of 140° C. to 180° C. Unfortunately, the monomer mixture produced by this commercial process is enriched in less valuable $CH_3SiCl_3$ relative to other more valuable monomers and the gravimetric ratio, $(CH_3SiCl_3/(CH_3)_2SiCl_2)$, is typically greater than 1.0.

Accordingly, an objective of the present invention is the provision of an enhanced process for preparing organohalosilane monomers from conventionally cleavable Direct Process Residue which does not involve the use of expensive noble catalysts, which provides reduced $R^1SiX_3$ and increased $R^1{}_2SiHX$, $R^1SiHX_2$ and $R^1{}_2SiX_2$ compared to conventional commercial processes such as tertiary amine catalyzed hydrochlorination, and which is easily conducted at moderate temperatures and relatively short reaction times.

SUMMARY OF THE INVENTION

In one aspect, the present invention is directed to a catalytic process for producing an organohalosilane monomer composition from a high-boiling residue resulting from the Direct Reaction of an organohalide with silicon, said process comprising (A) heating the high-boiling residue in the presence of a catalyst comprising (1) one or more heterocyclic amines and/or one or more heterocyclic ammonium halides, and (2) one or more quaternary Group 15 onium compounds, optionally in the presence of an organohalide and/or a hydrogen halide and/or an inert gas, at a temperature within the range of about 75° C. to about 300° C. under atmospheric pressure or superatmospheric pressure to convert the high-boiling residue to an organohalosilane monomer composition containing at least one organohalosilane monomer having a general formula selected from the group consisting of $R^1SiHX_2$, $R^1{}_2SiHX$, $R^1{}_2SiX_2$ and $R^1{}_3SiX$, $R^1$ being an aromatic, aliphatic, alkaryl or cycloaliphatic univalent hydrocarbyl group, X being a halogen atom selected from the group consisting of fluorine, chlorine, bromine, and iodine, and (B) optionally recovering the catalyst, wherein the high-boiling residue comprises (1) a cleavable component containing at least one of diorganotetrahalodisilanes and triorganotrihalodisilanes and (2) optionally an uncleavable component containing at least one of carbosilanes, organohalopolysilanes, hexaorganodisilanes, pentaorganohalodisilanes and tetraorganodihalodisilanes, with the proviso that if present, the uncleavable component has a concentration no greater than that of the cleavable component; and wherein the quaternary Group 15 onium compound is of the general formula, $R_4Q^+X^-$, wherein each R is independently an alkyl, cycloalkyl, aryl or alkaryl group of from 1 to 30 carbon atoms, Q is phosphorus, arsenic, antimony or bismuth, and X is a halide selected from the group consisting of F, Cl, Br and I.

The process of the invention is effective in converting the high-boiling residue to a organohalosilane monomer composition that is rich in compounds of the general formulae, $R^1SiHX_2$, $R^1{}_2SiHX$, $R^1{}_2SiX_2$, and $R^1{}_3SiX$ and deficient in compounds of the general formula $R^1SiX_3$ such that the gravimetric ratio of $R^1SiX_3$ to $R^1{}_2SiX_2$ is less than that obtained when the same high-boiling residue is similarly heated in the absence of a catalyst, or is subjected to a tertiary-amine catalyzed hydrochlorination. Advantageously, in the monomer composition produced by the present process, the gravimetric ratio of $R^1SiX_3$ to $R^1{}_2SiX_2$ is less than 1.0; and the gravimetric ratio of $(R^1SiHX_2 + R^1{}_2SiHX + R^1{}_2SiX_2 + R^1{}_3SiX)/R^1SiX_3$ is greater than 2.

DETAILED DESCRIPTION OF THE INVENTION

The present invention provides a process for converting a high-boiling residue resulting from the reaction of an organohalide, $R^1X$, with copper-activated silicon to useful organohalosilane monomers such as those of the general formulae, $R^1SiHX_2$, $R^1{}_2SiHX$, $R^1{}_3SiX$ and $R^1{}_2SiX_2$. As used herein, $R^1$ is an aromatic, aliphatic, alkaryl or cycloaliphatic univalent hydrocarbyl group and X is a halogen atom such as fluorine, chlorine, bromine or iodine. Examples of $R^1$ are methyl, ethyl, phenyl, cyclohexyl, allyl, vinyl and benzyl. Advantageously, the high-boiling residue is resulted from the Direct Reaction of methylchlorosilanes, ethylchlorosilanes, phenylchlorosilanes, methylbromosilanes, ethylbromosilanes, or phenylbromosilanes; and $R^1$ is methyl, ethyl or phenyl and X is chloride or bromide. More advantageously, $R^1$ is methyl and X is chloride. In one embodiment, the catalytic process of the invention provides an organohalosilane monomer composition containing $(CH_3)_2SiHCl$, $CH_3SiHCl_2$, $(CH_3)_3SiCl$, $(CH_3)_2SiCl_2$, and $CH_3SiCl_3$, wherein the content of $(CH_3)_2SiCl_2$ and $CH_3SiHCl_2$, individually or collectively, exceeds that of $CH_3SiCl_3$.

Suitable high-boiling residues contain a cleavable component and optionally an uncleavable component with the proviso that if present, the uncleavable component has a concentration no greater than that of the cleavable component.

As used herein, organohalodisilanes, organohalopolysilanes, and carbosilanes that are not converted to monomeric silanes by tertiary amine-catalyzed hydrochlorination are termed "uncleavable" or "conventionally uncleavable." Those that can be converted to monomeric silanes are called "cleavable" or "conventionally cleavable."

The cleavable component in the high-boiling residue contains at least one of diorganotetrahalodisilanes and triorganotrihalodisilanes. Suitable diorganotetrahalodisilanes are represented by the formulae: $X_2R^1SiSiR^1X_2$ and $XR^1{}_2SiSiX_3$. Suitable triorganotrihalodisilanes are represented by the formulae: $X_2R^1SiSiR^1{}_2X$ and $R^1{}_3SiSiX_3$. $R^1$ and X have the same meanings as defined above in the context of the organohalide and organohalosilane monomers. Exemplary diorganotetrahalodisilanes and triorganotrihalodisilanes include $Cl_2(CH_3)SiSi(CH_3)Cl_2$, $Cl(CH_3)_2SiSiCl_3$, $(CH_3)_3SiSiCl_3$ and $Cl_2(CH_3)SiSi(CH_3)_2Cl$.

The uncleavable component contains at least one of carbosilanes, organohalopolysilanes, hexaorganodisilanes, pentaorganohalodisilanes and tetraorganodihalodisilanes.

Carbosilanes have one or more methylene (—$CH_2$—) groups and are represented by the general formula, $R^1{}_hX_jSi$—$(CH_2)_w$—$SiX_kR^1{}_l$, wherein h, j, k and l are individually $\geq 0$ provided that h+j=3 and k+l=3, w$\geq$1, preferably 1-4, and $R^1$ and X have the same meanings as defined herein above for organohalosilane monomers. Examples of carbosilanes include compounds having the general formulae $R^1X_2Si$—$CH_2$—$SiXR^1{}_2$ and $R^1X_2Si$—$CH_2$—$CH_2$—$SiX_2R^1$ with $R^1$=$CH_3$ and X=Cl. Carbosilanes with a single —$CH_2$— group between the silicon atoms are also called silylmethylenes or disilamethanes.

Organohalopolysilanes are those of the formula $R^1{}_mX_qSi$—$(Si(R^1X))_n$—$SiX_qR^1{}_m$ wherein the subscripts m and q are individually $\geq 0$ with the sum of m+q=3, n is an integer greater than 2, $R^1$ and X have the same meanings as defined herein above for organohalosilane monomers.

The hexaorganodisilanes, pentaorganohalodisilanes and tetraorganodihalodisilanes are represented by the general formulae of $R^1{}_3SiSiR^1{}_3$, $XR^1{}_2SiSiR^1{}_3$ and $XR^1{}_2SiSiR^1{}_2X$ respectively, wherein $R^1$ and X have the same meanings as defined herein above. Examples of hexaorganodisilanes, pentaorganohalodisilanes and tetraorganodihalodisilanes include $(CH_3)_3SiSi(CH_3)_3$, $Cl(CH_3)_2SiSi(CH_3)_3$ and $Cl(CH_3)_2SiSi(CH_3)_2Cl$.

In the present process, the high-boiling liquid residue, as described above, is heated in the presence of a catalyst comprising (1) one or more heterocyclic amines, and/or one or more heterocyclic ammonium halides, and (2) one or more quaternary Group 15 onium compounds of the general formula, $R_4Q^+X^-$, wherein each R is independently an alkyl, cycloalkyl, aryl or alkaryl group of from 1 to 30 carbon atoms, Q is a Group 15 element such as phosphorus, arsenic, antimony and bismuth, and X is a halide atom such as F, Cl, Br or I. It is appreciated that the R groups are not necessarily all the same. The catalyst can be formed external to the reactor and later added to the reactor, or internal to the reactor by adding the individual components of the catalyst to the reactor directly. Similarly, the catalyst and the high-boiling residue can be combined outside the reactor or they may be added to it individually.

Conversion of the high-boiling residue into organohalosilane monomers comprises at least one of the chemical reactions selected from the group consisting of disproportionation, redistribution, silylene extrusion, and silylene insertion. When combined, the heterocyclic amines, and/or the heterocyclic ammonium halides and the quaternary Group 15 onium compounds exhibit polarity, basicity and nucleophilicity sufficient to effect the cleavage, redistribution and disproportionation of the conventionally cleavable disilanes and conventionally uncleavable components, if present, in the high-boiling residue and the redistribution and disproportionation of the initially formed monomeric silanes, so as to produce a commercially desirable monomer composition.

According to the instant invention, the heterocyclic amine component of the catalyst comprises a heterocyclic hydrocarbon having at least one nitrogen atom in at least one hydrocarbon ring, in which the positioning of the nitrogen ensures that the molecule exhibits polarity, basicity and nucleophilicity sufficient to effect the desired catalysis. The heterocyclic amines of the invention have at least one nitrogen atom in at least one 4- to 8-membered hydrocarbon ring, where the ring atoms adjacent to the nitrogen can be carbon or nitrogen and the hydrocarbon ring or rings are, independently of one another, aromatic or non-aromatic hydrocarbon rings.

The nitrogen in the hydrocarbon ring can also be bonded to H or to branched or linear alkyl groups, advantageously C1 to C6-alkyl; or to oxygen, halogen, trialkoxysilyl, or $NR'_2$, in which R' is H, linear or branched C1 to C6 alkyl, or trialkoxysilyl or two sigma and one pi bond in the ring, or the bridgehead to a further ring.

Depending on the bonding to the adjacent ring atoms, the carbon in the hydrocarbon ring can be mono- or disubstituted by H, linear or branched alkyl, advantageously C1 to C6 alkyl, halogen, oxygen, or $NR'_2$, in which R' is H, linear or branched C1 to C6 alkyl, or trialkoxysilyl or carry a further hydrocarbon ring system or it forms the bridgehead to a further ring system. The substituents can, independently of one another, be identical or different.

Nitrogen-containing heterocyclic hydrocarbons which are particularly suitable for the catalysts of the present invention are, for example, 5-membered rings having from 1 to 3 nitrogen atoms in the hydrocarbon ring, preferably imidazole, 1-methylimidazole, 2-methylimidazole, 2-ethylimidazole, 2-isopropyl-imidazole, 4-methylimidazole, 2,4-dimethylimidazole, 2-(2-imidazolyl)imidazole, 2-phenylimidazole, imidazoline, imidazolidine, pyrazole, 3-methylpyrazole, pyrrolidone, N-methylpyrrolidone, 1,3-dimethyl-2-imidazolidone or 1,2,3-triazole, 1,2,4-triazole or 6-membered rings having at least one nitrogen atom in the hydrocarbon ring, preferably 2,2'-bipyridine, 1,3-dimethyl-3,4,5,6-tetrahydro-2(1H)pyrimidone or N,N-dibutylpiperazine or polycyclic hydrocarbons having at least one nitrogen atom in the hydrocarbon ring, preferably benzimidazole, benzotriazole, Urotropin, 1,5,7-triazabicyclo[4.4.0]dec-5-ene, 1,8-diazabicyclo-[5.4.0]undec-7-ene, 1,5-diazabicyclo[4.3.0]non-5-ene, diazabicyclo-octane. 2-Methylimidazole and 4-methylimidazole are preferred compounds for the catalysts of the present invention. Also preferred are heterocyclic amines with pKa 6.9-7.9. pKa values of the amines are published in a variety of sources, including *Dissociation Constants of Organic Bases in Aqueous Solution* by D. D. Perrin., relevant portions of which are incorporated herein by reference. The pKa values of some specific heterocyclic amines are indicated in parentheses following the names: imidazole (pKa 6.95), 2-methylimidazole (pKa 7.85), and 4-methylimidazole (pKa 7.52). Commercial supplies of heterocyclic amines may contain a low percentage of impurities. For example, 2-methylimidazole may contain about 0.05 to about 5 weight percent of imidazole.

Nitrogen atoms in heterocyclic amines are trivalent. When one or more nitrogen atoms is quaternized (that is, tetravalent and positively charged), the compound is a heterocyclic ammonium compound. Thus, imidazoles become imidazolium compounds when the nitrogen atoms at positions 1 and 3 are quaternized. Examples are imidazole hydrochloride, 1-butyl-3-methylimidazolium chloride, 1-(3-cyanopropyl)-3-methylimidazolium chloride, 1-methylimidazolium chloride, and 1-octyl-3-hexylimidazolium bromide. Heterocyclic ammonium halides, such as the imidazolium halides, can be formed in situ during the practice of the instant invention in the case wherein hydrogen halide, for example, HCl or HBr, is present in the high-boiling residue. Alternatively, the heterocyclic ammonium halides can be generated intentionally via addition of gaseous hydrogen halides and organohalides to the heterocyclic amine. The addition can be in a separate synthetic preparation, or it can be done in situ in the catalytic reactor with the heterocyclic amine, optionally admixed with the quaternary Group 15 onium compound and/or the high-boiling liquid residue.

Ionic liquids refer to organic salts that are liquid at temperatures less than 100° C. See M. J. Earle, et al., in *Pure & Applied Chem.*, vol. 72 (2000) pp 1391-1398, which is fully incorporated herein by reference. Heterocyclic ammonium halides that are liquid at temperatures less than 100° C. fall within the definition of ionic liquids. Examples are 1,2-dimethyl-3-(n-propyl)-imidazolium chloride, 1-ethyl-3-methylimidazolium bromide, 1,2-dimethyl-3-(n-butyl) imidazolium chloride, 1-butyl-3-methyl-imidazolium chloride, 1-(3-cyanopropyl)-3-methyl-imidazolium chloride, and 1-methylimidazolium chloride. In one embodiment, the heterocyclic ammonium halide is an ionic liquid selected from the group consisting of 1-methylimidazolium chloride, 1-butyl-3-methylimidazolium chloride, and 1-(3-cyanopropyl)-3-methylimidazolium chloride.

Examples of quaternary Group 15 onium compounds are tetra(n-butyl)phosphonium chloride, tetra(n-butyl)phosphonium bromide, trihexyl(tetradecyl)phosphonium bromide, methyltri(isobutyl)phosphonium bromide, methyltri(isobutyl)phosphonium chloride, tetra(n-octyl)phosphonium chloride, tri(n-butyl)tetradecylphosphonium chloride, and octyltri(butyl)phosphonium chloride. Tetra(n-butyl)phosphonium chloride is a preferred component for the catalyst of the present invention.

Quaternary Group 15 onium compounds and mixtures thereof, which are liquid at temperatures below 100° C. fall within the definition of ionic liquids as defined by R. Sesto, et al., in *J. Organometallic Chem.*, vol. 690 (2005) pp 2836-2842, which is fully incorporated herein by reference. Examples of these ionic liquids are tri(hexyl)tetradecylphosphonium chloride (CYPHOS® IL 101), tetra(n-butyl)phosphonium bromide (CYPHOS® IL 163), tetra(n-butyl)phosphonium chloride (CYPHOS® IL 164), tri(n-butyl)tetradecylphosphonium chloride (CYPHOS® IL 167) and methyltri(isobutyl)phosphonium chloride. In one embodiment the instant catalytic process comprises use of quaternary Group 15 onium ionic liquids for the recovery of organohalosilane monomers from the high-boiling residue.

Commercial supplies of the quaternary Group 15 onium compounds are likely to contain low percentage amounts of the compounds of general formulae $R_3QHX$, and HX, in which R, Q and X have the same meanings as defined above in the context of quaternary Group 15 onium compounds. For example, tetra(n-butyl)phosphonium chloride, $(n-C_4H_9)_4PCl$, can contain about 0.05 to about 5 weight percent, specifically about 0.1 to about 1.0 weight percent of HCl and about 0.05 to about 5 weight percent, specifically about 0.1 to about 1.0 weight percent of $(n-C_4H_9)_3PHCl$.

Advantageously, the catalysts of the invention, which contain (1) heterocyclic amines and/or heterocyclic ammonium halides, and (2) quaternary Group 15 onium compounds, are liquid at temperatures less than 100° C. In general, they have low vapor pressures in the temperature range specified herein for converting the high-boiling residue to the organohalosilane monomer composition. If the individual components of the catalysts are liquid at temperatures less than 100° C., then they can be added together and mixed to prepare the desired compositions. If, however, one or more is solid, then, advantageously, the component melting below 100° C. is heated to obtain a liquid and the other(s) are later dissolved in it. Catalysts, which are liquid below 100° C., are illustrated in the examples below. Melting behavior of the catalysts of the invention can be investigated by visual observations of the catalysts during heating and cooling cycles as well as by differential scanning calorimetry (DSC) and similar techniques.

Catalytic cleavage, redistribution and disproportionation of the compounds in the high-boiling residue can be realized with the combinations of (1) heterocyclic amines and/or heterocyclic ammonium halides and (2) quaternary Group 15 onium compounds having a wide range of gravimetric and molar values. In one embodiment, the catalyst of the invention contains from about 0.01 weight percent to about 99.95 weight percent of (1) heterocyclic amines and/or heterocyclic ammonium halides and from about 0.05 weight percent to 99.9 weight percent of (2) quaternary Group 15 onium compounds based on the total weight of components (1) and (2). In one embodiment, the catalyst of the invention contains 5 wt % to 85 wt % of 2-methylimidazole and 95 wt % to 15 wt % of tetra(n-butyl)-phosphonium chloride based on the total weight of the 2-methylimidazole and the tetra(n-butyl)-phosphonium chloride. Advantageously, the weight ratio of the heterocyclic amines and/or the heterocyclic ammonium halides relative to the quaternary Group 15 onium compounds is from about 1:9 to about 9:1, more advantageously from about 1:3 to about 3:1. On a molar basis, in certain embodiments, it is desirable to have a molar excess of heterocyclic amines and/or heterocyclic ammonium halides relative to quaternary Group 15 onium compounds. Thus, in the case of tetra(n-butyl)phosphonium chloride and 2-methylimidazole, the molar ratio of the imidazole to the phosphonium chloride can be from 1.1 to 100, specifically 1.5 to 60 and more specifically 1.5 to 20.

The present process requires the presence of a "catalytic amount" of a catalyst as described above. By the term "catalytic amount" it is meant an amount of catalyst sufficient to facilitate the conversion of the high-boiling residue to monomeric organohalosilanes. A preferred catalytic amount is the amount that is sufficient to facilitate the conversion of the high-boiling residue to an organohalosilane monomer composition that is rich in compounds of the general formulae, $R^1SiHX_2$, $R^1_2SiHX$, $R^1_2SiX_2$, and $R^1_3SiX$ and deficient in compounds of the general formula $R^1SiX_3$ such that the gravimetric ratio of $R^1SiX_3$ to $R^1_2SiX_2$ is less than that obtained when the high-boiling residue is similarly heated in the absence of any catalyst, or is subjected to a tertiary-amine catalyzed hydrochlorination, and is preferably less than 1.0; and the gravimetric ratio of $(R^1SiHX_2+R^1_2SiHX+R^1_2SiX_2+R^1_3SiX)/R^1SiX_3$ is greater than 2. The optimum amount of the catalyst required will depend upon the catalyst used and the composition of the high-boiling residue. Such amounts can be determined experimentally by those skilled in the art. In the case of treating the high-boiling residue from the Direct Synthesis of methylchlorosilane, methylbromosilane, ethylchlorosilane or phenylchlorosilane, the total weight of the catalysts of the invention is 1 to 50 weight percent based on the weight of high-boiling residue charged to the reactor for batchwise operation. Advantageously, it is 5 to 25 weight percent and, more advantageously, 8 to 20 weight percent.

When recovery and reuse of the catalyst is practiced, multiple batches of high-boiling residue can be converted on a single catalyst charge. In this mode of operation, the ultimate catalyst usage, defined as 100×(weight of the catalyst/total weight of the high-boiling residue), can be as low as 5 weight percent, advantageously 1 weight percent, more advantageously as low as 0.1 weight percent.

Catalytic cleavage, redistribution and disproportionation of the compounds in the high-boiling residue is carried out in reactors that can be operated safely at high pressures and temperatures and that also have means for agitation of the reaction mixture. The reactors should also be suitable for contact with corrosive materials such as halo silanes and organohalosilanes. Suitable reactors include mechanically-stirred reactors and gas-sparged reactors. The reactions can also be conducted in a bubble column. The processes of the invention may be run in a batch or continuous mode. In one embodiment, the catalyst and the high-boiling residue are added first to the reactor. Optionally, organohalide (for example, methyl chloride) and/or hydrogen halide (for example, HCl or HBr, advantageously HCl) and/or an inert gas (for example, nitrogen or argon) is added until a predetermined pressure reading has been stably established. The predetermined pressure is advantageously less than or equal to the value indicative of saturation at the ambient temperature. The quantity of HCl to be charged is 0.1-10 grams per 100 grams of the high-boiling residue feed. Preferably, it is 0.3-1.5 grams per 100 grams of the high-boiling residue feed.

Next, the reactor is heated from ambient temperature to between about 75° C. and about 500° C., advantageously to between about 75° C. and about 300° C., more advantageously to between about 100° C. and about 280° C., to effect the catalysis leading to the formation of the organohalosilane monomer composition. The set temperature is maintained for periods of 1 to 600 minutes, specifically greater than about fifteen minutes up to about 4 hours to convert the high-boiling residue to the desired monomer composition. A preferred time is 30 minutes up to about 2 hours. When heating is discontinued, the reactor and its contents are allowed to cool to room temperature, or some other convenient value, to permit safe and efficient separation and recovery of the organohalosilane monomers from the reaction mixture. The retentate, which contains the catalyst and the compounds with normal boiling points higher than those of the organohalosilane monomers, is recharged with a fresh high-boiling residue and the process is repeated. This reuse and recycle of the original catalyst charge can be repeated many times.

In another embodiment, the process of the instant invention can be conducted at atmospheric pressure. When the process is operated at atmospheric pressure, organohalosilane monomers produced by the cleavage and redistribution/disproportionation reactions will be discharged from the reactor at temperatures at which they have significant vapor pressure. Typically, the reaction mixture is agitated and heated to from about 140 to about 250° C., advantageously from about 140 to about 180° C. Organohalide (for example, methyl chloride) and/or hydrogen halide (for example, HCl) is optionally injected for a brief period or for the entire duration of the experiment. Monomeric methylchlorosilanes have been observed to begin to distill over when the reactor temperature is in the range of from about 130° C. to about 150° C. Reactions at atmospheric pressure are continued until the organohalosilane monomers no longer distill over. Thereafter, the reactor is cooled to a temperature at which fresh high-boiling residue can be recharged safely and the catalysis is repeated with the retained catalyst.

As discussed above, the catalytic process of the invention can be conducted at atmospheric pressure or superatmospheric pressure. In one embodiment, superatmospheric pressures are generated autogenously when the reactor is closed during the process. The ultimate pressures attained depend on the molar quantity of reagents and products and the reaction temperature and can be up to 7 MPa. Under the closed conditions, the organohalosilanes can undergo further redistribution and disproportionation reactions. Accordingly, the product composition obtained under atmospheric pressure can be different from that produced autogenously. In particular, lower amounts of the compounds of formula, $R^1{}_2SiHX$ are obtained and more of $R^1{}_2SiX_2$ and $R^1SiHX_2$ under autogenous conditions. In one embodiment, at step (A) of the processes according to the invention, the high-boiling residue is heated under a superatmospheric pressure of up to 7 MPa at about 150° C. to about 250° C. for a period of 30 to 150 minutes.

When the operating pressure is atmospheric and reaction products are volatilized from the reactor, the vapors can be fractionated in one or more distillation columns for isolation of pure organohalosilane monomers. In another process variant, the vapors are condensed and the liquid recovered for subsequent fractional distillation. When the reactor is closed during the process, it can be cooled to allow the temperature and pressure to decrease to values that permit safe, quantitative recovery of the reaction products. Thus, the reactor may be cooled to room temperature or lower so that any residual pressure can be released safely and liquid reaction products can be recovered for distillation. Alternatively, the reactor can be vented to a fractionating column or condenser while the reactor is still hot and its contents are vaporous.

The catalyst of the invention can be recovered as a solid or liquid residue after volatilization of the reaction mixture. Additional starting materials can be added to this residue for another catalytic cycle. Multiple catalytic cycles are thereby possible. Overall, many batches of high-boiling residue resulting from the Direct Process can be treated with a single charge of catalyst. Thus, effective catalyst usage is less than ten weight percent and preferably 0.1 to about 5 weight percent based on the weight of the catalyst charged in the first cycle divided by the total weight of feedstock charged in all the cycles.

In one embodiment, the process of this invention is conducted continuously by injecting the high-boiling residue into the bottom of a heated reaction column containing the catalyst in liquid form, preferably an ionic liquid. The reaction column is maintained at about 100 to about 300° C. where the liquid catalyst is stable and components in the high-boiling residue resulting from the Direct Process residue can be converted to organohalosilane monomers. Advantageously, the high-boiling residue is heated, even to a vapor, prior to injection into the reaction column. The reaction column can be topped with a reflux column to separate the more volatile organohalosilane monomers from unreacted and/or higher boiling compounds in the reactor effluent.

The following examples are intended to illustrate, but in no way limit the scope of the present invention. All parts and percentages are by weight and all temperatures are in degrees Celsius unless explicitly stated otherwise.

EXAMPLES

In the examples, Me represents the methyl radical, $CH_3$, and Bu is butyl, $C_4H_9$.

Gas Chromatography (GC) was done on an HP5890 chromatograph with thermal conductivity detection. The column used for the analysis of the methylchlorosilane monomers was 30.48 cm×0.64 cm (12 ft×0.25 inch) stainless steel packed with 30 weight percent OV-210 on Chromosorb P AWDMCS 80/100 mesh. Separation conditions were those disclosed by L. G. *Hawkins in Catalyzed Direct Reactions of Silicon*, K. M. Lewis and D. G. Rethwisch, Editors, *Elsevier Science Publishers*, 1993, pp 189-205, which is fully incorporated herein by reference. A 30.48 cm×0.32 cm (12 ft×0.125 inch) stainless steel column packed with 20 weight percent OV-101 on Chromosorb WHP was used for the analysis of carbosilanes, disilanes and polysilanes.

Gas Chromatography/Mass Spectrometry (GC/MS) analyses were carried out with an Agilent 6890GC/5973 MSD instrument fitted with a 30 meter-long ZB5 (5% phenyl, 95% methylpolysiloxane) capillary column. Column inner diameter was 0.25 mm and film thickness was 2.5 µm. The carrier gas was helium with 200:1 injection split ratio. The injection port and GC/MS interface temperatures were 250° C. and 270° C., respectively. Injection volume was 1 µL The oven temperature was held at 50° C. for 2 minutes before it was raised at a rate of 8° C./min to 340° C., and then was held for 16 minutes. The mass spectrometer was operated in the EI (70 eV electron impact ionization) full scan (m/z 10-800) mode.

DSC (Differential Scanning calorimetry) measurements were made with a TA Instruments DSC Q100 calorimeter.

For NMR characterization, samples were analyzed with a Bruker AVANCE 600 Spectrometer operating at field strength of 14.1T. Protons ($^1$H's) resonate at 600 MHz at this field strength. Samples for $^{29}$Si NMR were prepared as a 25% to 30% by volume solution in $Cr(AcAc)_3/CDCl_3$ to a final Cr salt concentration of ~0.05M $Cr(AcAc)_3$. The solution was placed in a 10 mm NMR tube. Chemical shifts were externally referenced to tetramethylsilane (TMS). An inverse gated decoupling pulse sequence was used with a pulse width of 45-degrees for $^{29}$Si. A delay of 10 s was used between scans (AQ of 1.4 s). The data were processed using a LB of 2 Hz.

Materials used in the Examples are listed in Table 1 below.

TABLE 1

| Material NAME | SUPPLIER |
|---|---|
| 2-Methylimidazole, 99% purity | Aldrich |
| 2-Methylimidazole, 99% purity | BASF |
| 2-Methylimidazole, 98.5% purity (contains 1.5% imidazole) | BASF |
| 4-Methylimidazole, 98% purity | Aldrich |
| 1-Methylimidazole, 98% purity | Aldrich |
| 1,2,4-Triazole, 98% purity | Aldrich |
| Tetra(n-butyl)phosphonium Chloride 96% purity | Aldrich |
| 1-Methylimidazolium Chloride | Aldrich |
| 1-Butyl-3-Methylimidazolium Chloride | Aldrich |
| 1-(3-cyanopropyl)-3-methylimidazolium Chloride | Aldrich |
| CYPHOS ® 443 (Tetra (n-butyl)phosphonium chloride, 96%) | Cytec |
| CYPHOS ® IL 167 (aka CYPHOS ® 3453), Tri(n-butyl)tetradecyl phosphonium chloride | Cytec |
| CYPHOS ® IL 101 (Tri n-hexyl)tetradecylphosphonium chloride | Cytec |

TABLE 1-continued

| Material NAME | SUPPLIER |
|---|---|
| 1,2-Dichloro-1,1,2,2-tetramethyldisilane | Gelest |
| Direct Process Residues | Momentive |

Examples 1A, 1B and Comparative Examples 1C and 1D

Examples 1A and 1B illustrate the synergy afforded by catalysts comprising 2-methylimidazole and tetra(n-butyl) phosphonium chloride in the preparation of methylchlorosilane monomers from a Direct Process Residue sample containing more than 50 wt % of the methylchlorodisilanes, $Cl(CH_3)_2SiSi(CH_3)Cl_2$ and $Cl_2(CH_3)SiSi(CH_3)Cl_2$. All of the experiments of Examples 1A, 1B and Comparative Examples 1C and 1D were run autogenously in a 300 ml autoclave at 150° C. or 265° C. for 1 or 3 hours as shown in Table 3. The composition for the methylchlorodisilane feedstock used in Examples 1A, 1B and Comparative Examples 1C and 1D is shown in Table 2. The methylchlorodisilane feedstock was the fraction with normal boiling point 150-160° C. obtained by distillation of Direct Process Residue.

Examples 1A and 1B: The 300 ml autoclave was cleaned, dried and purged with nitrogen. It was then charged with catalyst ((n-$C_4H_9$)$_4$PCl (96% purity, Aldrich), 2-methylimidazole (99% purity, Aldrich)) and 20 g methylchlorodisilane feedstock. The autoclave was sealed; the stirrer was set at 150 rpm and heating was applied to attain the set temperature, which was maintained for 1 or 3 hours. The heating mantle was then removed and the autoclave allowed to cool to room temperature. The residual pressure was discharged slowly and the reactor opened to retrieve the reaction mixture. Maximum and residual pressures and reaction times are recorded in Table 3. GC analyses of the liquid reaction products are also reported in Table 3.

Comparative Example 1C was run following the teachings in U.S. Pat. No. 5,416,232 and in Herzog, et al., *J. Organometallic Chem.*, vol. 507 (1996) pp 221-228. Comparative Example 1D followed the teachings disclosed in U.S. Pat. No. 4,298,559, in Baney, et al., *Organometallics*, vol 2 (1983) pp 859-863 and in Garcia-Escomel, et al., *Inorganica Chimica Acta.*, vol. 350 (2003) pp 407-413.

TABLE 2

COMPOSITION OF THE METHYLCHLORODISILANE FEEDSTOCK USED IN EXAMPLES 1A, 1B AND COMPARATIVE EXAMPLES 1C AND 1D

| COMPOUND | Wt % | COMPOUND | Wt % |
|---|---|---|---|
| $MeSiCl_3$ | 4.75 | $Me_3SiSiMeCl_2$ | 4.32 |
| $Me_2SiCl_2$ | 2.77 | $ClMe_2SiSiMe_2Cl$ | 7.42 |
| $Me_3SiSiMe_2Cl$ | 7.06 | $Cl_2MeSiSiMe_2Cl$ | 45.36 |
| $ClMe_2SiOSiMe_2Cl$ | 2.01 | $Cl_2MeSiSiMeCl_2$ | 25.28 |
| $Cl_2MeSiOSiMe_2Cl$ | 1.02 | | |

TABLE 3

SUMMARY OF REACTION CONDITIONS AND ANALYTICAL DATA FOR EXAMPLES 1A, 1B AND COMPARATIVE EXAMPLES 1C AND 1D.

| | EX 1A | EX 1B | COMP EX 1C | COMP EX 1D |
|---|---|---|---|---|
| Catalyst | Bu$_4$PCl, 1.5 g + 2-MeIm, 0.5 g | Bu$_4$PCl, 1 g + 2-MeIm, 1 g | 2-MeIm, 2 g | Bu$_4$PCl, 2 g |
| Temp, ° C. | 265 | 150 | 150 | 150 |

TABLE 3-continued

SUMMARY OF REACTION CONDITIONS AND ANALYTICAL DATA FOR
EXAMPLES 1A, 1B AND COMPARATIVE EXAMPLES 1C AND 1D.

|  | EX 1A | EX 1B | COMP EX 1C | COMP EX 1D |
|---|---|---|---|---|
| Time, h | 3 | 3 | 1 | 1 |
| Max Press, kPa | 1806 | 614 | 517 | 482.6 |
| Residual Press, kPa | 151.7 | 124 | 34.5 | 48.3 |
| MeSiHCl$_2$ (MH), wt % | 16.12 | 18.10 | 16.86 | 11.68 |
| Me$_3$SiCl (M), wt % | 8.23 | 6.51 | 4.84 | 5.21 |
| MeSiCl$_3$ (T), wt % | 7.07 | 7.30 | 10.92 | 17.54 |
| Me$_2$SiCl$_2$ (D), wt % | 51.82 | 40.25 | 36.18 | 40.48 |
| HVS, wt % | 15.51 | 27.84 | 30.70 | 24.59 |
| T/D | 0.12 | 0.18 | 0.30 | 0.43 |

2MeIm = 2-Methylimidazole,
HVS = Higher Boilers (Methylchlorodisilanes, etc)

The results of the experiments of Examples 1A and 1B and comparative Examples 1C and 1D show that catalysts comprising combinations of 2-methylimidazole and tetra(n-butyl)phosphonium chloride produced methylchlorosilane monomer mixtures wherein the content of CH$_3$SiCl$_3$ and the T/D ratio were substantially reduced compared to those of the compositions produced by using either 2-methylimidazole or tetra(n-butyl)phosphonium chloride alone. There were also changes in CH$_3$SiHCl$_2$, (CH$_3$)$_3$SiCl and conversion (HVS) that were dependent on the ratio of 2-methylimidazole to tetra(n-butyl)phosphonium chloride as well as on reaction time and temperature.

Examples 2 to 14 and Comparative Examples 15, 16

The examples illustrate trends in the formation of methylchlorosilane monomers from a Direct Process Residue stream when reaction time, temperature and the ratio of 2-methylimidazole to tetra(n-butyl)phosphonium chloride were varied.

The feedstock used in Examples 2 to 14 and Comparative Examples 15 and 16 included compounds with normal boiling points up to about 200° C. It contained methylchlorotrisilanes and methylchlorocarbosilanes in addition to methylchlorodisilanes. The composition for the feedstock as determined by GC, GC/MS and $^{29}$Si NMR is shown in Table 4. GC analysis showed Monomers (5.28 area %), Disilanes (55.18 area %), Trisilanes and Carbosilanes (39.54 area %). From $^{29}$Si NMR analysis, Cl$_2$CH$_3$SiSi(CH$_3$)$_2$Cl accounted for 14.2 mole %, Cl$_2$CH$_3$SiSiCH$_3$Cl$_2$ for 29.9 mole %, Carbosilanes 33.2 mole % and Trisilanes for 8 mole %.

TABLE 4

COMPOUNDS IDENTIFIED IN DIRECT PROCESS
LIQUID USED IN EXAMPLES 2-16

| MONOMERS | (CH$_3$)$_2$SiCl$_2$, CH$_3$SiCl$_3$ |
|---|---|
| DISILANES | (CH$_3$)$_3$SiSi(CH$_3$)$_2$Cl, Cl(CH$_3$)$_2$SiSi(CH$_3$)$_2$Cl, Cl$_2$CH$_3$SiSi(CH$_3$)$_2$Cl, Cl$_2$CH$_3$SiSiCH$_3$Cl$_2$ |

TABLE 4-continued

COMPOUNDS IDENTIFIED IN DIRECT PROCESS
LIQUID USED IN EXAMPLES 2-16

| CARBO-SILANES | Cl(CH$_3$)$_2$SiCH$_2$Si(CH$_3$)$_2$Cl, Cl$_2$CH$_3$SiCH$_2$Si(CH$_3$)$_2$Cl, Cl$_2$CH$_3$SiCH$_2$SiCH$_3$Cl$_2$ |
|---|---|
| TRISILANES | Cl$_2$CH$_3$Si(CH$_3$SiCl)Si(CH$_3$)$_2$Cl, Cl$_2$CH$_3$Si(CH$_3$SiCl)SiCH$_3$Cl$_2$ |

Experiments were done in the 300 ml autoclave, described in Example 1, with 20 g Direct Process Residue and 2 g total catalyst ((n-C$_4$H$_9$)$_4$PCl (96% purity, Aldrich) and 2-methylimidazole (99% purity, Aldrich)). Reaction temperatures were either 150° C. or 265° C. Reaction times were measured from when the set temperature was attained and were recorded in Tables 5A to 5C. The 2-methylimidazole content of the catalyst composition (2-methylimidazole plus tetra(n-butyl)phosphonium chloride) was tested at 0, 25, 50, 75 and 100 weight percent. The experiments at the 2-methylimidazole concentration termini are the comparative Examples 15 and 16.

The experimental data for Examples 2 to 14 and Comparative Examples 15 and 16 are summarized in Tables 5A-5C. Analysis of the data involved plotting the reaction performance indices (D wt %, MH wt %, SUM/T, T/D, Conversion) on three-dimensional plots with temperature, time and 2-methylimidazole content of the catalyst composition as independent variables. Both MH wt % and SUM/T were at their highest values at 150° C., 1 hour reaction time and when 2-methylimidazole was greater than or equal to 50 weight percent of the catalyst composition, but less than 100 weight percent. D wt % was highest at 265° C. and reaction times longer than 1 hour. The lowest T/D values occurred most often when 2-methylimidazole was greater than or equal to 50 weight percent of the catalyst composition, but less than 100 weight percent, irrespective of the temperature and time. Highest conversions of the Direct Process Residue liquid to methylchlorosilane monomers were observed at 150° C., 1 hour reaction time and when 2-methylimidazole was 50 to 75 weight percent of the catalyst composition.

TABLE 5A

EXPERIMENTAL DATA FOR EXAMPLES 2-6

|  | EX 2 | EX 3 | EX 4 | EX 5 | EX 6 |
|---|---|---|---|---|---|
| Catalyst Composition, g | 2-MeIm, 0.5<br>Bu$_4$PCl, 1.5 | 2-MeIm, 1.0<br>Bu$_4$PCl, 1.0 | 2-MeIm, 1.5<br>Bu$_4$PCl, 0.5 | 2-MeIm, 0.5<br>Bu$_4$PCl, 1.5 | 2-MeIm, 1.0<br>Bu$_4$PCl, 1.0 |
| Temp, ° C. | 150 | 150 | 150 | 150 | 150 |

TABLE 5A-continued

EXPERIMENTAL DATA FOR EXAMPLES 2-6

|  | EX 2 | EX 3 | EX 4 | EX 5 | EX 6 |
|---|---|---|---|---|---|
| Time, h | 1 | 1 | 1 | 3 | 3 |
| Max Press, kPa | 68 psi | 82 psi | 76 psi | 72 psi | 83 psi |
| Residual Press, kPa | 5 psi | 4 psi | 5 psi | 7 psi | 6 psi |
| Liquid, g | 18.71 | 19.90 | 16.7 | 16.05 | 18.93 |
| Solid t, g | 0.18 | 0.5 | — | 0.85 | 0.6 |
| $Me_2SiHCl$ (M2H), wt % | 0.51 | 0.63 | 0.88 | 0.64 | 0.59 |
| $MeSiHCl_2$ (MH), wt % | 21.85 | 34.70 | 31.29 | 16.33 | 27.25 |
| $Me_3SiCl$ (M), wt % | 1.31 | 1.84 | 1.89 | 1.72 | 1.92 |
| $MeSiCl_3$ (T), wt % | 24.92 | 17.62 | 14.24 | 21.16 | 18.02 |
| $Me_2SiCl_2$ (D), wt % | 32.54 | 31.42 | 30.82 | 33.50 | 33.76 |
| HVS, wt % | 18.88 | 13.78 | 20.88 | 27.30 | 18.46 |
| T/D | 0.77 | 0.56 | 0.46 | 0.63 | 0.53 |
| SUM/T | 2.26 | 3.89 | 4.56 | 2.47 | 3.52 |
| CONV % | 77.83 | 84.99 | 77.68 | 66.81 | 79.20 |

2MeIm = 2-Methylimidazole,
HVS = Higher Boilers (Methylchlorodisilanes, etc)
(SUM/T) = (M2H + MH + M + D)/T

TABLE 5B

EXPERIMENTAL DATA FOR EXAMPLES 7 to 10 and COMPARATIVE EXAMPLE 15

|  | EX 7 | COMP EX 15 | EX 8 | EX 9 | EX 10 |
|---|---|---|---|---|---|
| Catalyst, g | 2-MeIm, 1.5 $Bu_4PCl$, 0.5 | 2-MeIm, 0 $Bu_4PCl$, 1.0 | 2-MeIm, 0.5 $Bu_4PCl$, 1.5 | 2-MeIm, 1.0 $Bu_4PCl$, 1.0 | 2-MeIm, 1.5 $Bu_4PCl$, 0.5 |
| Temp, °C. | 150 | 265 | 265 | 265 | 265 |
| Time, h | 3 | 3 | 3 | 3 | 3 |
| Max Press, KPa | 81 psi | 164 psi | 150 psi | 189 psi | 180 psi |
| Residual Press, kPa | 8 psi | 6 psi | 27 psi | 34 psi | 36 psi |
| Liquid Product, g | 17.97 |  | 10.88 | 9.74 | 8.12 |
| Solid Product, g | 0.04 |  | 6.92 | 8.5 | 9.27 |
| $Me_2SiHCl$ (M2H), wt % | 0.76 | 1.44 | 0.21 | 0.26 | 0.14 |
| $MeSiHCl_2$ (MH), wt % | 20.82 | 16.13 | 8.05 | 13.41 | 7.18 |
| $Me_3SiCl$ (M), wt % | 2.55 | 1.38 | 2.14 | 1.64 | 1.97 |
| $MeSiCl_3$ (T), wt % | 16.34 | 30.18 | 20.56 | 18.44 | 22.59 |
| $Me_2SiCl_2$ (D), wt % | 41.20 | 24.58 | 43.29 | 34.61 | 45.19 |
| HVS, wt % | 18.33 | 26.29 | 25.75 | 31.65 | 22.93 |
| T/D | 0.40 | 1.23 | 0.47 | 0.53 | 0.50 |
| SUM/T | 4.00 | 1.44 | 2.61 | 2.71 | 2.41 |
| CONV, % | 80.11 | 69.91 | 71.21 | 65.42 | 71.48 |

2MeIm = 2-Methylimidazole,
HVS = Higher Boilers (Methylchlorodisilanes, etc)
(SUM/T) = (M2H + MH + M + D)/T

TABLE 5C

EXPERIMENTAL DATA FOR EXAMPLES 11 to 14 and COMPARATIVE EXAMPLE 16

|  | COMP EX 16 | EX 11 | EX 12 | EX 13 | EX 14 |
|---|---|---|---|---|---|
| Catalyst, g | 2-MeIm, 1.0 $Bu_4PCl$, 0 | 2-MeIm, 0.5 $Bu_4PCl$, 1.5 | 2-MeIm, 0.5 $Bu_4PCl$, 1.5 | 2-MeIm, 1.0 $Bu_4PCl$, 1.0 | 2-MeIm, 1.5 $Bu_4PCl$, 0.5 |
| Temp, °C. | 265 | 265 | 265 | 265 | 265 |
| Time, h | 3 | 4 | 1 | 1 | 1 |
| Max Press, kPa | 191 psi | 204 psi | 152 psi | 172 psi | 156 psi |
| Residual Press, kPa | 21 psi | 27 psi | 23 psi | 25 psi | 26 psi |
| Liquid Product, g |  |  | 10.0 | 10.35 | 8.0 |
| Solid Product, g |  |  | 6.87 | 7.57 | 10.13 |
| $Me_2SiHCl$ (M2H), wt % | 1.33 | 0.31 | 0.58 | 0.25 | 0.52 |
| $MeSiHCl_2$ (MH), wt % | 27.18 | 20.28 | 10.11 | 11.68 | 16.19 |
| $Me_3SiCl$ (M), wt % | 1.48 | 1.72 | 2.32 | 1.48 | 1.95 |
| $MeSiCl_3$ (T), wt % | 23.12 | 23.62 | 28.50 | 15.35 | 19.23 |
| $Me_2SiCl_2$ (D), wt % | 26.77 | 35.10 | 49.08 | 35.02 | 34.23 |
| HVS, wt % | 20.11 | 18.97 | 9.42 | 36.21 | 27.88 |

TABLE 5C-continued

EXPERIMENTAL DATA FOR EXAMPLES 11
to 14 and COMPARATIVE EXAMPLE 16

|  | COMP EX 16 | EX 11 | EX 12 | EX 13 | EX 14 |
|---|---|---|---|---|---|
| T/D | 0.86 | 0.67 | 0.58 | 0.44 | 0.56 |
| SUM/T | 2.12 | 2.43 | 2.18 | 3.16 | 2.74 |
| CONV, % | 76.15 |  | 58.64 | 58.16 | 67.71 |

2MeIm = 2-Methylimidazole,
HVS = Higher Boilers (Methylchlorodisilanes, etc)
(SUM/T) = (M2H + MH + M + D)/T

Examples 17 to 20 and Comparative Example 21

These Examples illustrate cleavage of Direct Process Residue liquid to methylchlorosilane monomers with the use of HCl in combination with the 2-methylimidazole plus tetra (butyl)phosphonium chloride catalyst composition.

All experiments, except that of the Comparative Example 21, were done at 175° C. in the 300 ml autoclave already described herein. The composition of the feedstock is disclosed in Table 6. Note that $Cl_2MeSiSiMe_2Cl$ and $Cl_2MeSiSiMeCl_2$ amounted to 39.55 wt % and $Me_3SiSiMe_2Cl$ and $ClMe_2SiSiMe_2Cl$ to 12.76 wt %. Reaction times were varied from 0.5 to 2 hours. After the Direct Process Residue (DPR) and catalyst composition were charged to the reactor, HCl gas was introduced at room temperature to obtain steady-state values of 62 kPa (9 psig) or 137.9 kPa (20 psig) as indicated in Table 7. The HCl flow was then closed and the reactor heated to 175° C. and maintained at that temperature for the times shown in Table 7.

TABLE 6

COMPOSITION OF THE DIRECT PROCESS RESIDUE
FEEDSTOCK USED IN EXAMPLES 17 to 20
AND COMPARATIVE EXAMPLE 21

| COMPOUND | Wt % | COMPOUND | Wt % |
|---|---|---|---|
| $Me_3SiCl$ | 1.44 | $ClMe_2SiSiMe_2Cl$ | 8.69 |
| $MeSiCl_3$ | 9.56 | $Cl_2MeSiSiMe_2Cl$ | 19.01 |
| $Me_2SiCl_2$ | 32.53 | $Cl_2MeSiSiMeCl_2$ | 20.54 |
| $Me_3SiSiMe_2Cl$ | 4.08 | Siloxanes & Carbosilanes | 4.15 |

In Comparative Example 21, as taught in U.S. Pat. No. 2,709,176, the feedstock was treated in a 500 ml 3-necked round bottom flask, at atmospheric pressure and 85 to 175° C., with a continuous flow of HCl in the presence of a catalytic amount (10 g) of N,N-dimethyloctyl amine. Monomers formed were condensed and collected for subsequent analysis. HCl flow was discontinued after about 2.5 hr, when the overhead flow of reaction product had slowed to a trickle.

The product from the experiment of comparative Example 21, had T/D=0.99 and SUM/T=1.50. Products from the experiments of Examples 17-20 all had T/D less than 0.99 and SUM/T greater than 1.50. This means that the monomer composition obtained using a catalyst composition of this invention is higher in value than that produced via conventional, commercial, tertiary amine catalyzed hydrochlorination.

TABLE 7

EXPERIMENTAL DATA FOR EXAMPLES 17-20 AND COMPARATIVE EXAMPLE 21

|  | EX 17 | EX 18 | EX 19 | EX 20 | COMP EX 21 |
|---|---|---|---|---|---|
| Catalyst, g | 2-MeIm, 5.0 $Bu_4PCl$, 5.0 | 2-MeIm, 5.0 $Bu_4PCl$, 5.0 | 2-MeIm, 5.0 $Bu_4PCl$, 5.0 | 2-MeIm, 5.0 $Bu_4PCl$, 5.0 | N,N-dimethyloctyl amine, 10 |
| DPR, g | 100 | 100 | 100 | 106 | 105 |
| HCl Press, kPa | 62 | 137.9 | 137.9 | 137.9 |  |
| Temp, ° C. | 175 | 175 | 175 | 175 | 85-175 |
| Time, h | 1 | 0.5 | 1 | 2 | 2.25 |
| Max Press, kPa | 965 | 1034 | 1241 | 1275 | NA |
| Residual Press, kPa | 131 | 227.5 | 337.8 | 372 | NA |
| Liquid Product, g | 116.0 | 111.7 | 107.3 | 107.7 | 96.3 |
| Solid Product, g | 1.0 | 0.7 | 0.5 | 0.6 | — |
| $Me_2SiHCl$ (M2H), wt % | 0.60 | 0.66 | 0.64 | 0.87 | — |
| $MeSiHCl_2$ (MH), wt % | 19.34 | 20.73 | 25.12 | 25.48 | 16.61 |
| $Me_3SiCl$ (M), wt % | 1.36 | 1.32 | 1.51 | 1.61 | 1.68 |
| $MeSiCl_3$ (T), wt % | 27.11 | 27.33 | 22.15 | 19.80 | 37.34 |
| $Me_2SiCl_2$ (D), wt % | 43.70 | 42.61 | 43.32 | 44.79 | 37.82 |

TABLE 7-continued

EXPERIMENTAL DATA FOR EXAMPLES 17-20 AND COMPARATIVE EXAMPLE 21

|  | EX 17 | EX 18 | EX 19 | EX 20 | COMP EX 21 |
|---|---|---|---|---|---|
| HVS, wt % | 7.89 | 7.35 | 7.26 | 7.45 | 6.55 |
| T/D | 0.62 | 0.64 | 0.51 | 0.44 | 0.99 |
| SUM/T | 2.40 | 2.39 | 3.19 | 3.67 | 1.50 |
| CONV, % | 83.79 | 85.46 | 86.21 | 86.60 | — |

2MeIm = 2-Methylimidazole,
HVS = Higher Boilers (Methylchlorodisilanes, etc)
(SUM/T) = (M2H + MH + M + D)/T Among Examples 17-20, the use of HCl (0.01-0.03 mole) at 175° C. for 1 to 2 hours yielded optimum conversion, T/D and SUM/T values. Since the DPR feed sample contained an appreciable amount (32.53 wt %) $Me_2SiCl_2$, it was necessary to determine net formation of this monomer and the others in the reaction product. These values are shown in Table 8.

TABLE 8

NET FORMATION OF METHYLCHLOROSILANE MONOMERS IN EXPERIMENTS OF EXAMPLES 17-20

|  | EX 17 | EX 18 | EX 19 | EX 20 |
|---|---|---|---|---|
| M2H, g | 0.696 | 0.737 | 0.697 | 0.948 |
| MH, g | 22.434 | 23.155 | 26.954 | 27.442 |
| M, g | 0.138 | 0.034 | 0.191 | 0.208 |
| T, g | 21.888 | 20.968 | 14.207 | 11.191 |
| D, g | 18.162 | 15.065 | 13.952 | 13.757 |

The results show that there was net formation of all five methylchlorosilanes in all of the experiments. The data also show that net formation of $Me_2SiCl_2$ (D) and $MeSiCl_3$ (T) decreased, while $Me_2SiHCl$ (M2H) and $MeSiHCl_2$ (MH) increased with the changes in quantity of HCl charged and reaction times as indicated in Table 7.

Example 22

This example illustrates the cleavage of Direct Process Residue with a catalyst containing equal weights of 2-methylimidazole and tetra(n-butyl)-phosphonium chloride, wherein the catalyst is pre-melted to form a homogeneous mass prior to contact with the Direct Process Residue liquid.

Tetra(n-butyl)phosphonium chloride (5 g) was placed in a test tube and heated to 80° C. in an oil bath. 2-Methylimidazole (5 g) was slowly added to the resulting liquid whereupon it too melted. The hot liquid mixture was then transferred to the 300 ml autoclave. The molar ratio of 2-methylimidazole to tetra(n-butyl)phosphonium chloride was 3.59. Direct Process Residue (100 g) having the composition shown in Table 6 was added and the autoclave was sealed and pressurized with HCl up to 137.9 kPa (20 psig). Reaction was conducted at 175° C. for 1 hour. Maximum pressure attained was 1213 kPa (176 psig) and the residual pressure, on cooling, was 296 kPa (43 psig). After the headspace was vented, 107.8 g liquid and 1 g solid were recovered from the autoclave.

Table 9 summarizes the composition of the liquid determined by gas chromatography and the calculated net formation of methylchlorosilane monomers. The results are similar to those in Examples 19 and 20, with the exception that more $Me_2SiHCl$ was formed. It appears that combination of the quaternary onium compound and heterocyclic amine as liquids contributes to increased homogeneity of the catalytic composition and favors formation of $Me_2SiHCl$ as well as increased conversion of the Direct Process Residue.

TABLE 9

COMPOSITION OF LIQUID PRODUCT OF EXAMPLE 22 AND NET FORMATION OF METHYLCHLOROSILANES

|  | LIQUID COMPOSITION, wt % | NET FORMATION, g |
|---|---|---|
| $Me_2SiHCl$ (M2H) | 5.97 | 6.44 |
| $MeHSiCl_2$ (MH) | 23.56 | 25.40 |
| $Me_3SiCl$ (M) | 1.84 | 0.54 |
| $MeSiCl_3$ (T) | 20.29 | 12.31 |
| $Me_2SiCl_2$ (D) | 42.94 | 13.76 |
| HVS | 5.40 | −50.65 |
| T/D | 0.47 |  |
| SUM/T | 3.66 |  |
| CONV % | 89.69 |  |

Examples 23A and 23B

These Examples illustrate the use of a catalyst comprising terta(n-butyl) phosphonium chloride as the onium compound and imidazole as the heterocyclic amine. Both experiments were done in the 300 ml autoclave at 175° C. for 1 hour with 20 g Direct Process Residue having a composition shown in Table 6 and 1 g each terta(n-butyl) phosphonium chloride and imidazole. Example 23A was done with added HCl (137.9 kPa) and Example 23B without HCl.

TABLE 10

COMPOSITION OF LIQUID PRODUCTS OF EXAMPLE 23A AND EXAMPLE 23B

|  | EXAMPLE 23A | EXAMPLE 23B |
|---|---|---|
| $MeHSiCl_2$ (MH), wt % | 0.83 | 0.16 |
| $Me_3SiCl$ (M), wt % | 3.25 | 3.39 |
| $MeSiCl_3$ (T), wt % | 18.28 | 12.26 |
| $Me_2SiCl_2$ (D), wt % | 66.47 | 76.90 |
| HVS, wt % | 11.17 | 7.29 |
| T/D | 0.28 | 0.16 |
| SUM/T | 3.86 | 6.56 |
| CONV % | 90.51 | 90.64 |

The compositions of the liquid products from both experiments are summarized in Table 10. 9.60 g of liquid and 8.30 g solid were recovered from Example 23A and 14.50 g liquid and 2.7 g solid from Example 23B. Conversions were both >90%. The product mixtures contained more $Me_2SiCl_2$ and less $MeHSiCl_2$ than those obtained with 2-methylimidazole and tetra(n-butyl)phosphonium chloride.

Examples 24A and 24B

These Examples illustrate catalytic cleavage of Direct Process Residue wherein the quaternary onium compound of the catalytic composition is tri(n-butyl)tetradecyl phosphonium chloride or tri(n-hexyl)tetradecyl phosphonium chloride. Tri(n-butyl)tetradecyl phosphonium chloride (CYPHOS® IL 167 also known as CYTEC® 3453) has a molecular weight of 435.15 and melting point of 45° C. Tri(n-hexyl)tetradecyl phosphonium chloride (CYPHOS® IL 101) is liquid at ambient temperature. Its molecular weight is 519.31.

In the experiment of Example 24A, 20 g of the Direct Process Residue of Table 6 was reacted with a catalyst consisting of 1 g ($1.22 \times 10^{-2}$ mole) 2-methylimidazole and 1 g ($2.29 \times 10^{-3}$ mole) tri(n-butyl)tetradecyl phosphonium chloride in the 300 ml PARR autoclave as described in Example 1 at 175° C. for 1 hour. Maximum pressure was 930 kPa.

The experiment of Example 24B was run with 20 g of the Direct Process Residue of Table 6 using a catalyst consisting of 1 g ($1.22 \times 10^{-2}$ mole) 2-methylimidazole and 1 g ($1.93 \times 10^{-3}$ mole)tri(n-hexyl)tetradecyl phosphonium chloride under the same conditions. Maximum pressure was 862 kPa. The experimental results are summarized in Table 12.

TABLE 12

COMPOSITION OF LIQUID PRODUCTS
OF EXAMPLE 24A AND EXAMPLE 24B

| | EXAMPLE 24A | EXAMPLE 24B |
|---|---|---|
| Catalyst | 2-Methylimidazole and $(n-C_4H_9)_3C_{14}H_{29}PCl$ | 2-Methylimidazole and $(n-C_6H_{13})_3C_{14}H_{29}PCl$ |
| Product Weight, g | 17.4 g liquid | 15.3 g liquid |
| | 6.1 g solid | 4.2 g solid |
| $Me_2SiHCl$ (M2H), wt % | 5.39 | 10.41 |
| $MeHSiCl_2$ (MH), wt % | 19.43 | 23.84 |
| $Me_3SiCl$ (M), wt % | 2.98 | 2.56 |
| $MeSiCl_3$ (T), wt % | 11.60 | 11.69 |
| $Me_2SiCl_2$ (D), wt % | 53.27 | 44.72 |
| HVS, wt % | 7.33 | 6.78 |
| T/D | 0.22 | 0.26 |
| SUM/T | 6.99 | 6.97 |
| CONV % | 88.71 | 90.82 |

The data show that both catalysts afforded high (>88%) conversions of the Direct Process Residue to commercially valuable methylchlorosilane monomers, as indicated by the T/D (0.22 and 0.26) and SUM/T (6.99 and 6.97) values.

Examples 25A-25C

These Examples illustrate recycle and reuse of a catalyst consisting of 2-methylimidazole and tetra(n-butyl)phosphonium chloride, at a 1:1 weight ratio, for the cleavage of the Direct Process Residue of Table 6.

The experiment of EXAMPLE 25A was started by melting 5 g tetra(n-butyl)phosphonium chloride (CYPHOS® 443) in a test tube at ~80° C. and adding 5 g 2-methylimidazole to it. The liquid was transferred to the 300 ml Parr autoclave along with 100 g Direct Process Residue (see Table 6). HCl (75.8 kPa at 23° C.) was charged; and the reaction mixture was heated to 175° C. and maintained there for 1 hour. The maximum pressure was 1144 kPa (166 psig). Residual pressure was 110 kPa on cooling the reactor back to room temperature. After release of the pressure, the total weight of the reaction product was 110.7 g. After GC analysis, 84.14 g liquid was decanted from the reactor and subjected to rotary evaporation in vacuo for removal of the methylchlorosilane monomers. 60 g liquid was condensed in the trap and 24 g residue retained in the flask. The liquid condensed in the trap was analyzed by gas chromatography.

The second catalytic cleavage (EXAMPLE 25B) was done with the 26 g reaction mixture retained in the autoclave (EXAMPLE 25A) and 111.84 g Direct Process Residue. HCl (137.8 kPa at 23° C.) was charged. No additional catalyst was introduced. Again, the reactor was heated to 175° C. and maintained at that temperature for 1 hour. Maximum pressure was 820 kPa and residual pressure, on cooling, was 152 kPa. The liquid product was analyzed by gas chromatography.

A third cleavage reaction (EXAMPLE 25C) was done with 113 g Direct Process Residue and the 24 g residue from the rotovap separation described above. No additional catalyst was introduced. HCl (137.8 kPa at 23° C.) was charged and the reactor heated to 175° C. and maintained at that temperature for 1 hour. Maximum pressure was 1006 kPa and residual pressure, on cooling, was 138 kPa. The liquid product was analyzed by gas chromatography.

Altogether, 324.8 g Direct Process Residue was treated with 10 g total catalyst to obtain 282.64 g liquid product, 259.98 g of which were methylchlorosilane monomers. Catalyst usage was 3.1 wt %. Monomer yield was 92% of the product and 80% based on the Direct Process Residue charged. Table 13 shows the total weights of each monomer and the net amounts formed in the catalyst reuse experiment. Conversion of the methylchlorodisilanes, trisilanes and carbosilanes is indicated by the negative value of the HVS in the table.

TABLE 13

CALCULATED METHYLCHLOROSILANE FORMATION
IN THE CATALYST REUSE EXPERIMENTS
OF EXAMPLES 25A-25C

| | TOTAL WEIGHTS FROM THREE REACTIONS, g | NET MONOMER FORMATION, g |
|---|---|---|
| $Me_2SiHCl$ (M2H) | 7.98 | 7.98 |
| $MeHSiCl_2$ (MH) | 45.76 | 45.76 |
| $Me_3SiCl$ (M) | 5.26 | 0.58 |
| $MeSiCl_3$ (T) | 74.17 | 43.12 |
| $Me_2SiCl_2$ (D) | 126.81 | 21.14 |
| HVS | 22.65 | (−160.79) |

T/D ratio in the accumulated product was 0.58 and SUM/T was 2.50. In contrast, hydrochlorination of the same Direct Process Residue using N,N-dimethyloctyl amine as a catalyst yielded a product with T/D ratio 0.99 and SUM/T 1.50 as shown in Comparative Example 21.

Examples 26A to 26C

These Examples illustrate recycle and reuse of a catalyst consisting of 2-methylimidazole and tetra(n-butyl)phosphonium chloride, at a 1:1 weight ratio, for the cleavage of the Direct Process Residue of Table 14.

The initial experiment (EXAMPLE 26A) was done in the 300 ml Parr autoclave at 175° C. for 1 hour with 100 g Direct Process Residue and a molten mixture containing 5 g each of 2-methylimidazole and tetra(n-butyl)phosphonium chloride. No HCl was charged in this step. Maximum pressure attained was 958 kPa. After 1 hour at 175° C., heating was discontinued. The vent valve for the reactor headspace was connected to a trap chilled in dry-ice/isopropanol. The valve was opened when the reactor cooled to 100° C. to transfer the volatile reaction products to the trap. 44.3 g product was recovered in this way. It was analyzed by gas chromatography. The reactor was cooled to room temperature for introduction of the second charge of Direct Process Residue.

For EXAMPLE 26B, an additional 100 g Direct Process Residue was added to the 65.7 g of material retained in the reactor from EXAMPLE 26A. No additional catalyst was introduced. The reactor was pressurized with HCl (137.8 kPa at 23 C) and heated again to 175° C. for 1 hour. Thereafter, it was cooled to 125° C. before the vent valve was opened to transfer the product as just described above. 92.7 g product was recovered from the trap. It was then analyzed by gas chromatography. Again, the reactor was cooled to room temperature for addition of the third charge of raw material.

For EXAMPLE 26C, 100 g Direct Process Residue was added to the 39.7 g retained in reactor. No additional catalyst was introduced. The reactor was pressurized with HCl (137.8 kPa at 23° C.) and heated again to 175° C. for 1 hour. Thereafter, it was cooled to 150° C. before the vent valve was opened to transfer the product as just described above. 124.67 g liquid was recovered from the trap. 32 g liquid was recovered from the reactor after it had been cooled to room temperature. Both samples were analyzed by gas chromatography.

The data summary on methylchlorosilane formation is set forth in Table 15. Altogether 261.7 g reaction product was recovered in the traps from the catalytic cleavage of 300 g Direct Process Residue. Methylchlorosilane monomers accounted for 215.0 g: a 72% yield based on the weight of Direct Process Residue charged. Net monomer formation was 186.9 g.

T/D ratio in the accumulated product was 0.61 and SUM/T was 3.01. In contrast, hydrochlorination of the same Direct Process Residue using tributylamine (9 wt % based on the weight of feed) as catalyst yielded a product with T/D ratio 0.72 and SUM/T 2.09.

TABLE 14

COMPOSITION OF THE DIRECT PROCESS RESIDUE
FEEDSTOCK USED IN EXAMPLES 26A to 26C

| COMPOUND | Wt % | COMPOUND | Wt % |
|---|---|---|---|
| MeSiHCl$_2$ | 1.53 | ClMe$_2$SiSiMe$_2$Cl | 11.13 |
| Me$_2$SiCl$_2$ | 7.83 | Cl$_2$MeSiSiMe$_2$Cl | 25.29 |
| Me$_3$SiSiMe$_3$ | 0.79 | Cl$_2$MeSiSiMeCl$_2$ | 23.32 |
| Me$_3$SiSiMe$_2$Cl | 7.35 | Siloxanes, Trisilanes & Carbosilanes | 22.77 |

TABLE 15

CALCULATED METHYLCHLOROSILANE FORMATION
IN THE CATALYST REUSE EXPERIMENTS
OF EXAMPLES 26A to 26C

| | TOTAL WEIGHTS FROM THREE REACTIONS, g | NET MONOMER FORMATION, g |
|---|---|---|
| Me$_2$SiHCl (M2H) | 14.54 | 14.54 |
| MeHSiCl$_2$ (MH) | 54.35 | 49.76 |
| Me$_3$SiCl (M) | 5.07 | 5.07 |
| MeSiCl$_3$ (T) | 53.57 | 53.57 |
| Me$_2$SiCl$_2$ (D) | 87.43 | 63.95 |
| HVS | 46.71 | (−225.21) |

Examples 27A to 27C

These Examples illustrate recycle and reuse of a catalyst consisting of 2-methylimidazole and tetra(n-butyl)phosphonium chloride, at a 3:1 weight ratio, for the cleavage of the Direct Process Residue of Table 16.

EXAMPLE 27A was done in the 300 ml Parr autoclave at 175° C. for 1 hour with 20 g Direct Process Residue, 1.5 g 2-methylimidazole, 0.5 g tetra(n-butyl)-phosphonium chloride and HCl (137.8 kPa at 23° C.). Maximum pressure attained was 537.6 kPa. After 1 hour at 175° C., heating was discontinued; and the reactor was cooled to room temperature. Residual pressure (27.6 kPa) was then vented; and the reactor opened. 15 g liquid was withdrawn by pipette and analyzed by gas chromatography. The remaining liquid and solids were used in EXAMPLE 27B.

For EXAMPLE 27B, another 20 g Direct Process Residue and HCl(137 kPa at 23° C.) were charged to the retained reaction mixture from Example 27A in the reactor and the experiment continued at 175° C. for 1 hour with no more added catalyst. Maximum pressure was 579 kPa and the residual was 48 kPa after the reactor was cooled to room temperature. 20 g liquid was withdrawn for analysis after the reactor had been vented and opened.

EXAMPLE 27C was run at 175° C. for 1 hour with retained reaction mixture from Example 27B, 20 g more Direct Process Residue, HCl (137.8 kPa at 23° C.) and no additional catalyst. Maximum pressure was 558 kPa and residual pressure was 55 kPa. 26 g liquid was pipetted from the reactor.

TABLE 16

COMPOSITION OF THE DIRECT PROCESS RESIDUE
FEEDSTOCK USED IN EXAMPLES 27A to 27C

| COMPOUND | Wt % | COMPOUND | Wt % |
|---|---|---|---|
| Me$_3$SiCl | 0.80 | ClMe$_2$SiSiMe$_2$Cl | 9.41 |
| MeSiCl$_3$ | 0.72 | Cl$_2$MeSiSiMe$_2$Cl | 43.63 |
| Me$_2$SiCl$_2$ | 11.65 | Cl$_2$MeSiSiMeCl$_2$ | 32.71 |
| Me$_3$SiSiMe$_2$Cl | 1.08 | | |

Tables 17 and 18 summarize the analytical data for the three reaction mixtures. In Table 17, conversion was calculated by subtracting the HVS Area % of the sample from that of the starting material (87.32%) and dividing the result by 87.32 Area %. The data show that conversion of the methylchlorodisilanes was greater than 73% for the three charges tested. Overall, catalyst usage was 2.5 wt % of the feedstock.

TABLE 17

CONVERSION OF FOUR CHARGES OF DIRECT
PROCESS RESIDUE WITH A SINGLE CHARGE
(10 wt %) IN EXAMPLES 27A-27C

| MOMOMERS, AREA % | | HIGHER BOILERS, AREA % | |
|---|---|---|---|
| 12.68 | | 87.32 | |
| FEEDSTOCK CHARGE | MOMOMERS, AREA % | HIGHER BOILERS, AREA % | CONVERSION, % |
| EX 27A, 20 g | 79.87 | 19.09 | 78.14 |
| EX 27B, 20 g | 82.17 | 16.87 | 80.68 |
| EX 27C, 20 g | 76.61 | 23.22 | 73.40 |

Total weight (48.33 g) of the methylchlorosilane monomers formed from the three experiments was calculated from the GC analysis and the weights of recovered reaction products. Monomer yield was 80.55 wt % based on the 60 g total feedstock charged. Table 18 shows the composition of the monomers.

TABLE 18

COMPSOITION OF THE METHYLCHLOROSILANE MONOMER
PRODUCT PRODUCED IN EXAMPLES 27A-27C

| | |
|---|---|
| $Me_2SiHCl$, wt % | 0.39 |
| $MeHSiCl_2$, wt % | 20.78 |
| $Me_3SiCl$, wt % | 2.10 |
| $MeSiCl_3$, wt % | 31.95 |
| $Me_2SiCl_2$, wt % | 44.78 |
| T/D | 0.71 |
| SUM/T | 2.13 |

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

The invention claimed is:

1. A catalytic process for producing an organohalosilane monomer composition from a high-boiling residue resulting from the Direct Reaction of an organohalide with silicon, said process comprising
   (A) heating the high-boiling residue in the presence of a catalyst comprising (1) one or more heterocyclic amines and/or one or more heterocyclic ammonium halides, and (2) one or more quaternary Group 15 onium compounds, optionally in the presence of an organohalide and/or a hydrogen halide and/or an inert gas, at a temperature within the range of about 75° C. to about 300° C. under atmospheric pressure or superatmospheric pressure
   to convert the high-boiling residue to an organohalosilane monomer composition containing at least one organohalosilane monomer having a general formula selected from the group consisting of $R^1SiHX_2$, $R^1_2SiHX$, $R^1_2SiX_2$ and $R^1_3SiX$, $R^1$ being an aromatic, aliphatic, alkaryl or cycloaliphatic univalent hydrocarbyl group, X being a halogen atom selected from the group consisting of fluorine, chlorine, bromine, and iodine, and
   (B) optionally recovering the catalyst,
   wherein the high-boiling residue comprises (1) a cleavable component containing at least one of diorganotetrahalodisilanes and triorganotrihalodisilanes and (2) optionally an uncleavable component containing at least one of carbosilanes, polysilanes, hexaorganodisilanes, pentaorganohalodisilanes and tetraorganodihalodisilanes, with the proviso that if present, the uncleavable component has a concentration no greater than that of the cleavable component; and
      wherein the quaternary Group 15 onium compound is of the general formula, $R_4Q^+X^-$, wherein each R is independently an alkyl, cycloalkyl, aryl or alkaryl group of from 1 to 30 carbon atoms, Q is phosphorus, arsenic, antimony or bismuth, and X is a halide selected from the group consisting of F, Cl, Br and I.

2. The process of claim 1 wherein the heterocyclic amine has at least one nitrogen atom in at least one 4- to 8-membered hydrocarbon ring, wherein the ring atoms adjacent to the nitrogen are carbon or nitrogen, and the hydrocarbon ring or rings are, independently of one another, aromatic or non-aromatic hydrocarbon rings.

3. The process of claim 2 wherein the heterocyclic amine has a pKa of about 6.9 to about 7.9.

4. The process of claim 2 wherein the heterocyclic amine contains a five-membered ring with 1 to 3 nitrogen atoms.

5. The process of claim 4 wherein the heterocyclic amine is selected from the group consisting of imidazole, 1-methylimidazole, 2-methylimidazole, 2-ethylimidazole, 2-isopropyl-imidazole, 4-methylimidazole, 2,4-dimethylimidazole, 2-(2-imidazolyl)imidazole, 2-phenylimidazole, imidazoline, imidazolidine, pyrazole, 3-methylpyrazole, pyrrolidone, N-methylpyrrolidone, 1,3-dimethyl-2-imidazolidone, 1,2,3-triazole, and 1,2,4-triazole.

6. The process of claim 1 wherein the heterocyclic ammonium halide is derived from a heterocyclic amine having at least one nitrogen atom in at least one 4- to 8-membered hydrocarbon ring, wherein the ring atoms adjacent to the nitrogen are independently carbon or nitrogen atoms, and the hydrocarbon ring or rings are, independently of one another, aromatic or non-aromatic hydrocarbon rings, wherein the halide is fluoride, chloride, bromide or iodide.

7. The process of claim 6 wherein the heterocyclic ammonium halide is derived from a heterocyclic amine with 1 to 3 nitrogen atoms in a five-membered ring, and the halide is fluoride, chloride, bromide or iodide.

8. The process of claim 7 wherein the heterocyclic ammonium halide is 1,2-dimethyl-3-(n-propyl)-imidazolium chloride, 1-ethyl-3-methylimidazolium bromide, 1,2-dimethyl-3-(n-butyl)imidazolium chloride, 1-butyl-3-methyl-imidazolium chloride, 1-(3-cyanopropyl)-3-methylimidazolium chloride, or 1-methylimidazolium chloride.

9. The process of claim 6 wherein the heterocyclic ammonium halide is an ionic liquid selected from the group consisting of 1-methylimidazolium chloride, 1-butyl-3-methylimidazolium chloride, and 1-(3-cyanopropyl)-3-methylimidazolium chloride.

10. The process of claim 1 wherein the quaternary Group 15 onium compound, $R_4Q^+X^-$, is tetra(n-butyl)phosphonium chloride, tetra(n-butyl)phosphonium bromide, trihexyl(tetradecyl)phosphonium bromide, methyltri(isobutyl)phosphonium bromide, methyltri(isobutyl)phosphonium chloride, tetra(n-octyl)phosphonium chloride, tri(n-butyl)tetradecylphosphonium chloride, or octyltri(butyl)phosphonium chloride.

11. The process of claim 10 wherein the quaternary Group 15 onium compound is an ionic liquid selected from the group consisting of tri(n-hexyl)tetradecylphosphonium chloride, tetra(n-butyl)phosphonium bromide, tetra(n-butyl)phosphonium chloride, tri(n-butyl)tetradecylphosphonium chloride, and methyltri(isobutyl)phosphonium chloride.

12. The process of claim 1 wherein the step (A) is conducted in the presence of an organohalide being methyl chloride or methyl bromide.

13. The process of claim 1 wherein the step (A) is conducted in the presence of a hydrogen halide being HCl or HBr.

14. The process of claim 1 wherein the step (A) is conducted in the presence of an inert gas being nitrogen or argon.

15. The process of claim 1 wherein the high-boiling residue resulted from the Direct Reaction of methylchlorosilanes, ethylchlorosilanes, phenylchlorosilanes, methylbromosilanes, ethylbromosilanes or phenylbromosilanes; and wherein $R^1$ is methyl, ethyl or phenyl and X is chloride or bromide.

16. The process of claim 1 wherein the gravimetric ratio $(R^1SiHX_2+R^1_2SiHX+R^1_2SiX_2+R^1_3SiX)/R^1SiX_3$ is greater than or equal to 2.

17. The process of claim 1 wherein the organohalosilane monomer composition comprises $(CH_3)_2SiHCl$, $CH_3SiHCl_2$, $(CH_3)_3SiCl$, $(CH_3)_2SiCl_2$, and $CH_3SiCl_3$, and wherein the content of $(CH_3)_2SiCl_2$ and $CH_3SiHCl_2$, individually or collectively, exceeds that of $CH_3SiCl_3$.

18. The process of claim 1 wherein the high-boiling residue is heated under a superatmospheric pressure of up to 7 MPa at about 150° C. to about 250° C. for a period of 30 to 150 minutes.

19. The process of claim 1 wherein the high-boiling residue is heated under ambient atmospheric pressure at about 140° C. to about 250° C.

20. The process of claim 1 wherein the catalyst comprises from about 0.01 wt % to about 99.95 wt % of (1) the heterocyclic amine and/or heterocyclic ammonium halide; and from about 0.05 wt % to about 99.9 wt % of (2) the quaternary Group 15 onium compound based on the total weight of components (1) and (2).

21. The process of claim 20 wherein the weight ratio of the heterocyclic amine and/or heterocyclic ammonium halide relative to the quaternary Group 15 onium compound is from about 1:9 to about 9:1.

22. The process of claim 21 wherein the catalyst comprises 2-methylmidazole and tetra(n-butyl)phosphonium and wherein the molar ratio of 2-methylmidazole to tetra(n-butyl) phosphonium chloride is from 1.1 to 100.

23. The process of claim 1 wherein the weight of the catalyst is 1 to 50 percent of the weight of the high-boiling residue.

24. The process of claim 1 wherein multiple batches of the high-boiling residue are converted to the organohalosilane monomer composition on a single catalyst charge, and the ultimate catalyst usage, defined as 100×(weight of the catalyst/total weight of the high-boiling residue), is about 0.1 to about 5 weight percent.

25. The process of claim 1 wherein the catalytic process comprises at least one reaction selected from the group consisting of disproportionation, redistribution, silylene extrusion, and silylene insertion.

26. The process of claim 25 wherein the reactions are conducted batchwise or continuously in ionic liquids in a mechanically-stirred reactor, a gas-sparged reactor or a bubble column.

* * * * *